United States Patent [19]

Shaw

[11] Patent Number: 4,806,356

[45] Date of Patent: Feb. 21, 1989

[54] TOBACCO PRODUCT

[76] Inventor: Alec S. W. Shaw, Birch House, Off Crimbles Lane, Cockerham, Lancashire, England

[21] Appl. No.: 35,274

[22] Filed: Apr. 3, 1987

Related U.S. Application Data

[63] Continuation of Ser. No. 873,141, Jun. 6, 1986, abandoned, which is a continuation of Ser. No. 792,201, Oct. 28, 1985, abandoned, which is a continuation of Ser. No. 625,544, Jun. 28, 1984, abandoned.

[30] Foreign Application Priority Data

Jun. 29, 1983 [GB] United Kingdom ............ 8317576

[51] Int. Cl.$^4$ ................. A61K 9/20; A61K 31/465
[52] U.S. Cl. ................. 424/440; 424/465; 514/356; 514/948; 514/960
[58] Field of Search ............. 514/948, 960, 356; 424/440, 464

[56] References Cited

U.S. PATENT DOCUMENTS

| | | | |
|---|---|---|---|
| 1,888,997 | 11/1932 | McLane | 424/264 |
| 2,033,495 | 3/1936 | Taylor et al. | 424/264 |
| 2,036,638 | 4/1936 | Lindstaedt | 424/264 |
| 2,086,766 | 7/1937 | Chuck | 424/264 |
| 2,091,840 | 8/1937 | Turnbow | 424/264 |
| 2,159,953 | 5/1939 | Proetto | 424/264 |
| 2,175,980 | 10/1939 | Turnbow | 424/264 |
| 2,811,499 | 10/1957 | Geary | 424/264 |
| 3,048,520 | 6/1962 | McKennis et al. | 424/264 |
| 3,071,509 | 1/1963 | O'Neill | 424/264 |
| 3,368,567 | 2/1968 | Speer | 424/264 |
| 3,845,217 | 10/1974 | Ferno et al. | 426/3 |
| 3,851,069 | 11/1974 | Hachtman | 426/175 |
| 3,870,794 | 3/1975 | Hutchinson et al. | 424/264 |
| 4,276,890 | 7/1981 | Fichera | 424/48 |
| 4,317,837 | 3/1982 | Kehoe et al. | 426/3 |

FOREIGN PATENT DOCUMENTS

| | | | |
|---|---|---|---|
| 632599 | 5/1963 | Belgium . | |
| 1000581 | 11/1976 | Canada | 424/48 |
| 524158 | 7/1940 | United Kingdom . | |
| 924052 | 4/1963 | United Kingdom . | |
| 1325011 | 8/1973 | United Kingdom | 424/48 |
| 2125699A | 3/1984 | United Kingdom | 424/48 |
| WO83/02892 | 1/1983 | World Int. Prop. O. | 424/48 |

OTHER PUBLICATIONS

Wesnes et al., Pharmacology & Therapeutics 21(2), 189-208, (1983), Smoking Nicotine and Human Performance.

Wesnes et al., The Effects of Cigarette Smoking and Nicotine Tablets Upon Human Attention in Thornton, Re(ed), "Smoking Behavior, Physiological and Psychological Influenies", Churchill, Livingstone, Goinburgn, (Wm 1765615).

Amure Vision Research, 18(10), 1449-1551, (1978), Nicotine and the Decay of the McCollough Effect.

Schmidt Munchener Medizinische Wochenschript 116(11): 557-564, Mar. 15, 1974.

Little et al., "Tablet Making", Northern Pub. Co. Ltd., Liverpool, Eng. 2nd Ed., (1963), pp. 11-13, 50-53, 139-140, Confectionery Tablets, Peppermint Tablet.

Jarboe et al., Chem. Abstracts 554 25942e, (1961), of J. Chem. Soc., (1961), 2455-2458, "Volatile Products of Pyrolysis of Nicotine".

Schmidt Munchener Medizinsche Wochenschrift 116(11): 557-564, Mar. 15, 1974, (Data-Base Print-Out).

Wesnes et al., Pharmacology and Therapeutics 21(2): 189-208, (1983), (Data-Base Print-Out).

Amure Vision Research 18(10): 1449-1531, (1978), (Data-Base Print-Out).

Warburton et al., pp. 19-43 and Wesnes et al., pp. 131-143, (1978), (Data-Base Print-Out) both in Thornton Re(editor), Smoking Behavior Physiological and Psychological Influences.

The Extra Pharmacopoeia Martindale, 28th Edition 1982, pp. 1732-1733, Re: "Nicotine".

The Pharmaceutical Codex, 11th Edition, 1979, p. 501, Re: "Lozenges", and pp. 906-908.

*Primary Examiner*—Shep K. Rose
*Attorney, Agent, or Firm*—Oblon, Fisher, Spivak, McClelland & Maier

[57] ABSTRACT

There is disclosed a nicotine containing lozenge prepared from a mixture of inert filler material, a binder and either pure nicotine or a nicotine containing substance by a technique not involving any application of heat. Cold compression in a conventional tablet making machine is preferred.

4 Claims, No Drawings

TOBACCO PRODUCT

This application is a continuation of application Ser. No. 873,141, filed June 6, 1986, now abandoned, which was a continuation of applicaton Ser. No. 792,201, filed Oct. 28, 1985, now abandoned, which was a continuation Ser. No. 625,544, filed June 28, 1984, now abandoned.

This invention concerns a tobacco product, and more particularly a nicotine containing lozenge which can be dissolved in the mouth to satisfy a craving for tobacco, either as an aid in stopping the habit of smoking or as a substitute for cigarettes or other smokable tobacco products in areas where smoking is dangerous or prohibited.

Previous attempts to produce a nicotine containing lozenge have generally failed, since such attempts have followed traditional confectionery making practice involving the production of a hot syrup which has caused the highly volatile nicotine oils to escape.

The present invention is based upon an appreciation of the possibility of producing a nicotine containing lozenge utilising the techniques customarily employed for the production of peppermints.

According to the present invention there is provided a method for the production of nicotine containing lozenges comprising the steps of thoroughly mixing together an inert filler, a binder and either pure nicotine or a nicotine containing substance and forming measured doses of the mixture into tablets by any process not involving the application of heat.

Preferably the tablet forming process is one of cold compression wherein the measured dose is compressed and shaped between movable dies. Other possibilities include extrusion or simply the drying out of doses of mixture initially in a paste-like form.

Generally flavouring agents and possibly colouring agents will be included in the mixture.

The invention also includes lozenges prepared by the methods aforesaid.

The invention will be further apparent from the following description which concerns, by way of example only, a variety of possible mixes from which lozenges may be prepared in accordance with the invention.

All lozenges embodying the invention are prepared from a mixture of inert filler material, a binder and either pure nicotine or a nicotine containing substance.

THE FILLER

The possibilities for the inert filler which will generally itself be a mixture of numerous ingredients are numerous.

A preferred formulation is:
Icing sugar: 4800 gms
Lactose: 2720 gms
Corn starch: 400 gms
Cocoa powder: 720 gms
Liquorice powder: 880 gms
Acacia powder: 400 gms
Tragacanth: 10 gms
Totalling: 9930 gms.

Numerous variations on this particular formulation are, however, possible. For example, some, for instance 800 gms, of the icing sugar may be replaced by dextrose. Again, for example, the relative proportions of cocoa powder and liquorice powder may be varied.

Generally, the exact formulation will be determined by the end taste and texture desired.

THE BINDER

Again the possibilities for the binder are limitless.
A basic formulation is:
Water: 1 litre
Acacia powder: 250 mls.

Amongst possible variations are, for example, the addition of one or more of the following:
Tragacanth, for instance: 30 gms
Coffee powder, for instance 600 gms
Malic or other fruit acid—neutralised with an hydroxide, for instance: 50 gms.

The water used in the preparation of the binder may first be simmered for 20 minutes or so with 100 gms of dried dill seeds or other herb or plant if desired.

THE NICOTINE PREPARATION

The nicotine is preferably present as pure nicotine dissolved in 40 ml of alcohol. The alcohol may be Absolute or a commercially available liqueur or spirit such as Crème de Menthe, Grand Marnier, whisky or rum, for example. The quantity of nicotine used is such as to give between 0.1 and 8mg per lozenge, preferably in the range of from 1 to 2 mg per lozenge. The nicotine preparation may be flavoured as desired with oil of peppermint, wintergreen, spearmint or methol, for example.

The nicotine may, however, be present as whole tobacco or a tobacco extract and such need not be admixed with alcohol or the other taste additives mentioned.

The filler and binder are thoroughly mixed, dried and passed through a screen to remove all lumps or the like. The nicotine preparation is dispersed into the mixture which is then formed into lozenges of desired size, preferably using cold compression tablet forming machinery of known kind.

The resultant lozenges dissolve slowly in the mouth releasing the contained nicotine gradually for absorption within the buccal cavity.

It will be appreciated that it is not intended to limit the invention to the above example only, many variations, such as might readily occur to one skilled in the art, being possible, without departing from the scope thereof as defined by the appended claims.

For example, other additives such as stimulants, for instance caffeine, may be included if desired.

Other filler materials might be used including, for example, magnesium stearate, sodium alginate, sodium pectate, a cellulose product such as methyl cellulose and starches.

I claim:
1. A method for satisfying a craving for tobacco by releasing a measured dose of nicotine gradually for absorption into the buccal cavity from a cold-compressed nicotine-containing lozenge tablet prepared by a method for the production of a nicotine-containing lozenge tablet comprising the steps of thoroughly mixing together an inert filler, a binder and pure nicotine dissolved in alcohol and forming measured doses of the mixture by a cold-compression tablet forming process wherein the lozenge tablet is compressed and shaped between movable dies.

2. The method according to claim 1, wherein the filler is predominantly comprised by one or more sugars.

3. The method according to claim 1, wherein the binder is comprised by an aqueous solution.

4. The method according to claim 1, wherein the binder includes acacia powder.

* * * * *